United States Patent [19]
Zwislocki

[11] Patent Number: 5,824,967
[45] Date of Patent: Oct. 20, 1998

[54] EAR MUFFLER

[75] Inventor: Jozef J. Zwislocki, Cazenovia, N.Y.

[73] Assignee: Syracuse University, Syracuse, N.Y.

[21] Appl. No.: 963,123

[22] Filed: Oct. 28, 1997

Related U.S. Application Data

[63] Continuation-in-part of Ser. No. 744,732, Oct. 29, 1996, abandoned.

[51] Int. Cl.$^6$ .................................................. H04R 25/02
[52] U.S. Cl. .......................................... 181/130; 181/135
[58] Field of Search .................................... 181/129, 130, 181/131, 135; 381/183, 187; 2/209; 128/864, 867

[56] References Cited

U.S. PATENT DOCUMENTS

| | | |
|---|---|---|
| 2,545,731 | 6/1951 | French . |
| 3,565,069 | 2/1971 | Miller . |
| 3,851,123 | 11/1974 | Lipinski et al. . |
| 3,863,028 | 1/1975 | Fixler . |
| 3,939,310 | 2/1976 | Hodges . |
| 4,006,796 | 2/1977 | Coehorst . |
| 4,110,583 | 8/1978 | Lepper . |
| 4,173,715 | 11/1979 | Gosman . |
| 4,387,784 | 6/1983 | Hill ......................................... 181/131 |
| 4,418,787 | 12/1983 | Eggert et al. . |
| 4,424,880 | 1/1984 | Murayama et al. . |
| 4,441,576 | 4/1984 | Allen . |
| 4,807,612 | 2/1989 | Carlson . |
| 4,852,683 | 8/1989 | Killion . |
| 4,864,610 | 9/1989 | Stevens .................................... 181/130 |
| 4,972,488 | 11/1990 | Weiss . |
| 5,022,486 | 6/1991 | Miura et al. ............................ 381/187 |
| 5,113,967 | 5/1992 | Killion et al. . |
| 5,276,740 | 1/1994 | Inanaga et al. ......................... 381/187 |

Primary Examiner—Khanh Dang
Attorney, Agent, or Firm—Wall Marjama Bilinski & Burr

[57] ABSTRACT

An ear muffler device suitable for coupling to the entrance of the ear canal of a person to reduce the level of ambient noise in the ear canal. The device includes a muffler tube of appropriate dimensions sufficient to isolate the ear canal from ambient air and having an inner cross-sectional area of at least approximately 1.15 cm$^2$ so as to substantially reduce the acoustic impedance at the entrance of the ear canal over a wide range of audible sound frequencies. A connecting tube for attachment to the ear canal is coupled to the ear muffler tube. Resilient sealing means adapted to seal the connecting tube to the ear canal are attached to the open end of the connecting tube. The device further includes means for securing it in the ear. A sound source isolated from ambient air may be attached near the end of the muffler tube.

22 Claims, 6 Drawing Sheets

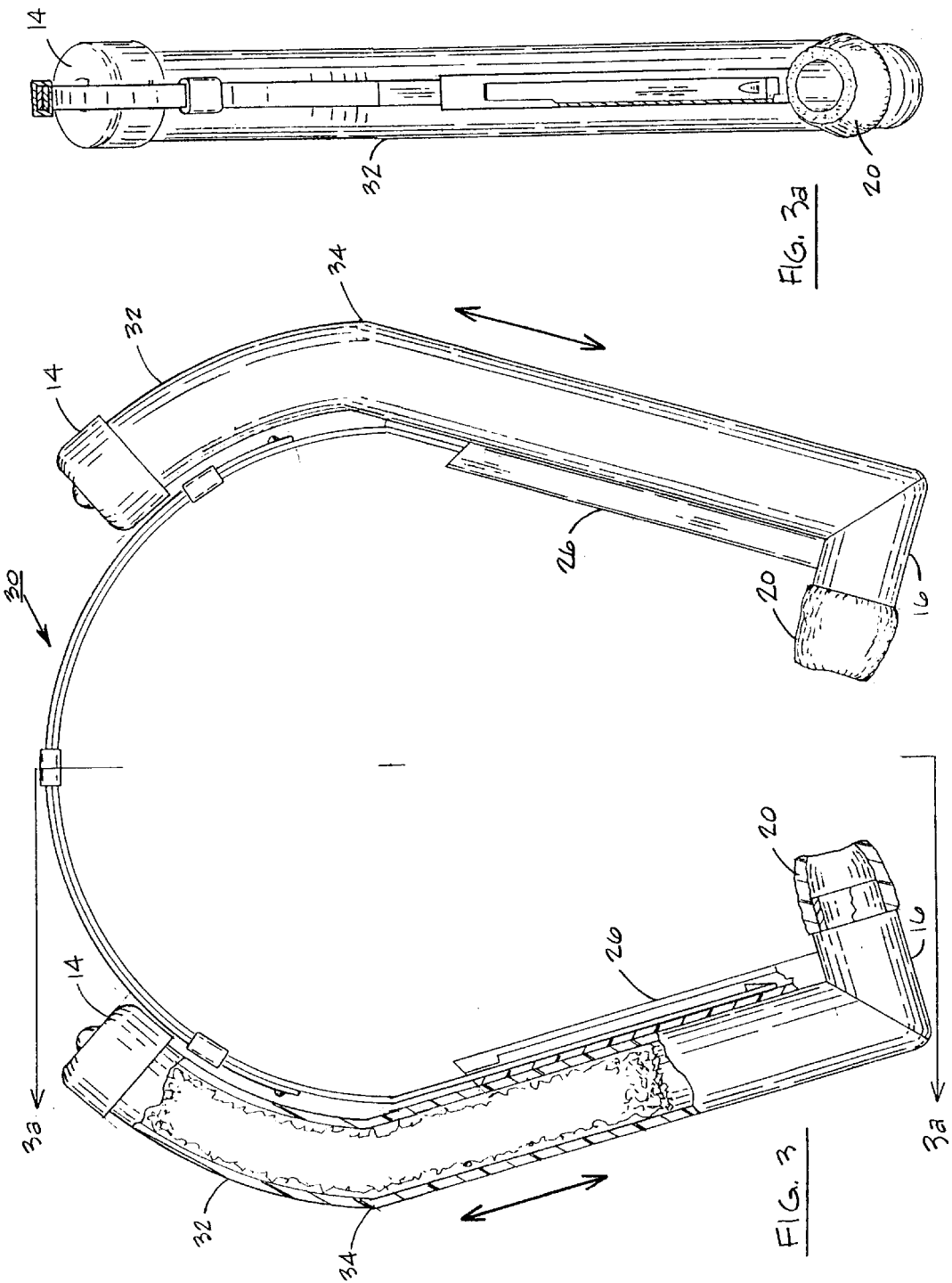

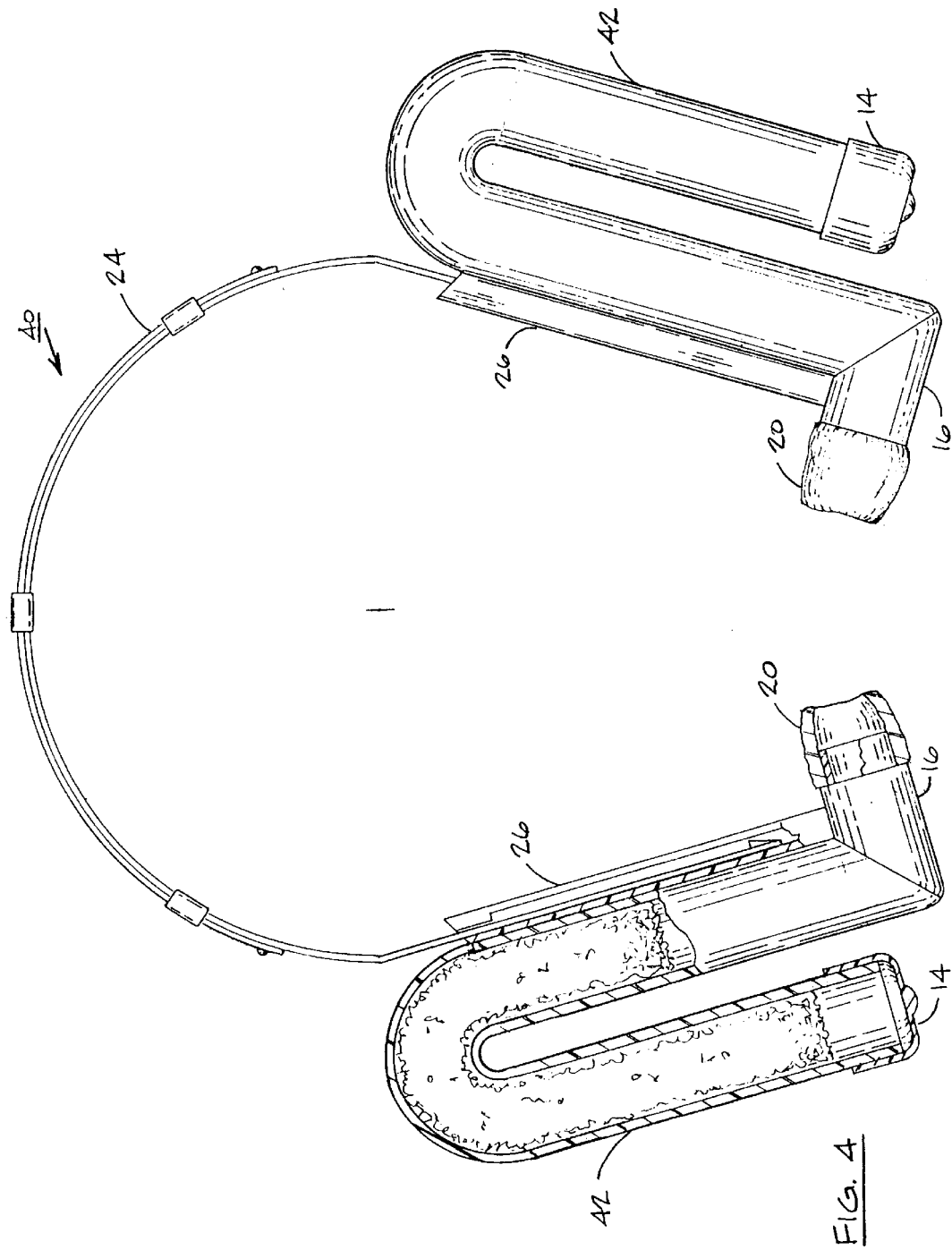

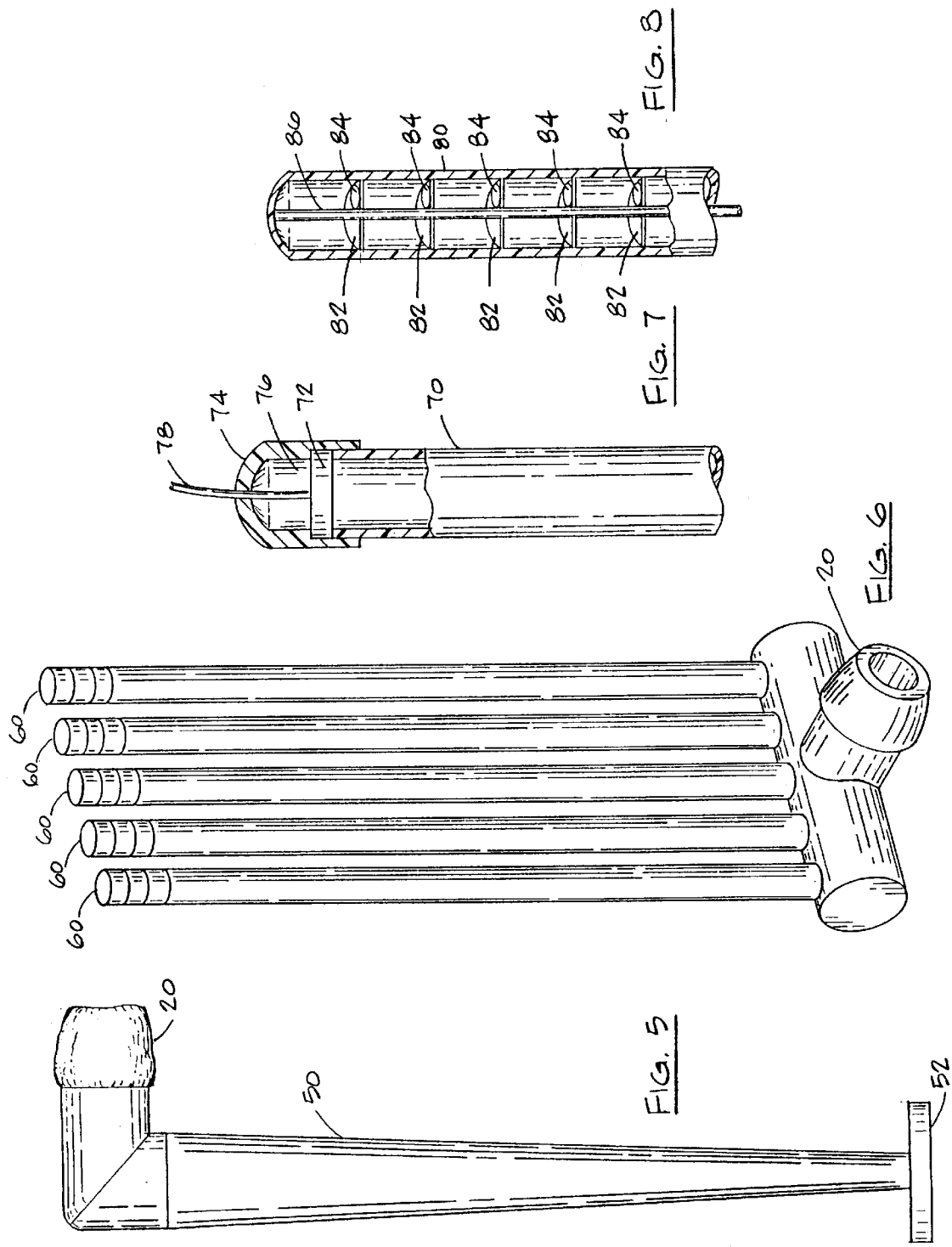

EAR MUFFLER

This application is a continuation-in-part of application Ser. No. 08/744,732 filed Oct. 29, 1996, now abandoned.

BACKGROUND OF THE INVENTION

The present invention relates to the reduction of ambient noise in the ear canal for the purpose of protecting the ear against damage, decreasing the fatiguing effect of unwanted noise, and improving communication through earphones and related devices. More specifically, the invention is directed at an ear defender of the semi-insert type, which is equipped with a tube of appropriate dimensions for each ear, therefore, called the "muffler tube", said tube being in air communication with the ear canal and tightly acoustically coupled to it with the help of an appropriate sealing device. When the ear muffler is used in combination with an earphone, or another sound-emitting device, it reduces the masking effect of unwanted environmental sounds on useful signals, such as speech, and improves in this way auditory communication.

Conventional prior art devices that protect or defend the ear against excessive noise can be divided into three classes: ear plugs, ear muffs and semi-inserts. Ear plugs are inserted into the ear canal; ear muffs cover the entire outer ear and are held in place by appropriate support means, such as a head band; semi-inserts are held against the entrance of the ear canal by means similar to those used for ear muffs. Each class of the devices has its advantages and disadvantages.

Ear plugs can provide substantial noise reduction (attenuation) distributed reasonably evenly over the audible frequency range of sound. They are small and inexpensive. However, they may cause discomfort in the ear canal. They also pose some hygiene problems resulting from ear wax and the possibility of introducing into the sensitive ear canal harmful substances that can produce irritation and infection of the ear canal walls. Further, there is the problem of fitting the individual ear canals which vary in size and shape over a wide range.

Ear muffs may provide the highest noise attenuation at sound frequencies exceeding 1000 Hz but are generically inferior to ear plugs at lower frequencies. Although these frequencies appear to be less damaging for the ear, they produce relatively strong masking of useful signals, such as speech, and can have a fatiguing effect. Because of their size, conventional ear muffs are cumbersome and become uncomfortable when worn for prolonged periods of time. They exert pressure on the sides of the head and have a bothersome warming effect on the head. Also, they are more expensive than the ear defenders in the remaining two classes.

Available semi-inserts reduce the problems of individual fit and hygiene inherent in the ear plugs and are less cumbersome and less expensive than ear muffs but tend to provide less noise attenuation. Attempts at improving the effectiveness of semi-inserts made in the past have led to increased pressure on the periphery of the ear canal and resulting discomfort.

A noteworthy variant of earplugs under the designation "resonator earplugs" became known in the past. These earplugs consisted of perforated ear inserts equipped with a small external enclosure in air communication with the ear canal. Acoustic interaction between the perforation and the enclosure produced a resonance effect that increased sound attenuation in the broad vicinity of the resonance frequency. In practice, the earplugs proved not to be satisfactory because of the protruding enclosure walls and the necessity of fitting them to the shape of the outer ear so as to make the necessary ear-insert perforation as short as possible. Otherwise, the resonance occurred at too low a frequency and produced a decreased sound attenuation at higher frequencies. For the same reasons, the size of the enclosure had to be made relatively small with the resulting limitation on achievable sound attenuation at low sound frequencies.

OBJECTS AND SUMMARY OF THE INVENTION

Accordingly, it is the object of the present invention to provide a semi-insert ear defender, called the ear muffler, with improved noise attenuation, achieved without increasing the necessary pressure on the soft tissues surrounding the entrance of the ear canal and without appreciably increasing the bulk and cost of the device.

It is a further object of the present invention to provide a semi insert ear defender, having increased noise attenuation achieved through a muffler tube of appropriate dimensions open at one end and closed at the other.

It is a further object of the present invention to provide a semi insert ear defender having increased noise attenuation that is achieved through a muffler tube having a substantially lower acoustic impedance at its open end than the acoustic input impedance of the ear canal over a wide frequency range.

It is still a further object of the present invention to achieve the low acoustic impedance at the open end of the muffler tube relative to the acoustic input impedance at the entrance of the ear canal by making the inner cross sectional area of the tube substantially greater than the cross sectional area of the ear canal.

It is still a further object of the present invention to achieve the low acoustic impedance at the open end of the muffler tube relative to the acoustic input impedance at the entrance of the ear canal by making the tube length equal to a quarter wavelength of sound at a desired frequency so as to produce a quarter wave resonance.

It is still another object of the present invention to control the sharpness of the quarter wave resonance by providing a muffler tube at least partially filled with lightly sound absorbing material.

It is still another object of the present invention to connect the muffler tube to the ear canal through a connecting tube that provides a tight acoustic coupling between the tube and the ear canal and that does not alter destructively the effect of the muffler tube.

It is another object of the present invention to provide an ear muffler with improved noise attenuation that is adaptable to given noise environments and communication needs.

It is a further object of the present invention to provide an ear muffler having increased noise attenuation, which includes communication capability for speech, music and other useful signals.

According to the present invention, there is provided a semi-insert ear defender that exhibits increased noise attenuation compared to available semi-insert devices, achieved through a muffler tube of appropriate dimensions having an open end and a closed end, the open end being coupled tightly acoustically to the ear canal with the help of a resilient sealing cuff. The muffler tube must be of appropriate dimensions to have a substantially lower acoustic impedance at its open end than the acoustic impedance at the entrance of the ear canal over a wide range of audible sound frequencies. In one preferred embodiment, the tube should have an inner cross sectional area of at least proximately 1.15 cm², but preferably greater, and a length of between 4 and 25 cm to sufficiently reduce the acoustic impedance at the ear canal entrance and usefully increase the sound attenuation at the ear over a satisfactory frequency range. In one embodiment, the tube is filled at least partially with lightly sound absorbing material.

BRIEF DESCRIPTION OF THE DRAWINGS

For a fuller understanding of the nature and objects of the invention, reference should be made to the following detailed description of a preferred mode of the present invention, read in connection with the accompanying drawings, in which:

FIG. 1a is a view of FIG. 1 taken along line 1a—1a.

FIG. 3 is a front partial sectional view of a second embodiment of an ear muffler device of the present invention.

FIG. 3a is a view of FIG. 3 taken along line 3a—3a.

FIG. 4 is a front partial sectional view of a third embodiment of an ear muffler device of the present invention.

FIG. 5 is a side view of a further embodiment of a modified muffler tube of the present invention.

FIG. 6 is a perspective view of a further embodiment of a modified muffler tube of the present invention.

FIG. 7 illustrates schematically a modified muffler tube structure having an electro-acoustic transducer or an equivalent component placed at the end of the muffler tube.

FIG. 8 illustrates a muffler tube which contains an internal acoustic network.

DETAILED DESCRIPTION OF THE INVENTION

Figure 1:
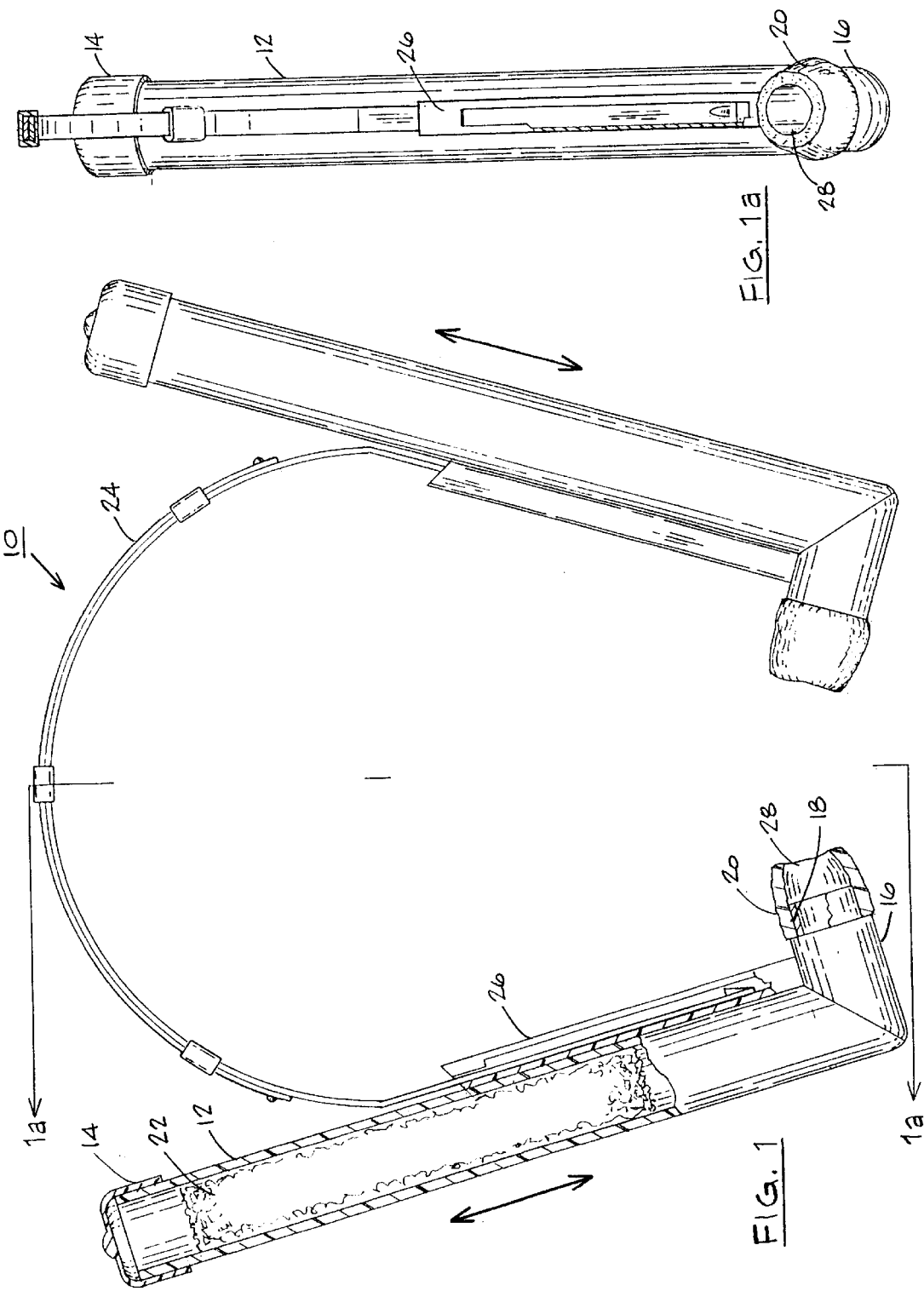
FIG. 1 is a front partial sectional view of an ear muffler device of the present invention.

The object of the present invention is to increase the effectiveness of semi insert ear defenders in reducing the level of ambient noise in the ear canal. As can be understood by those skilled in the art, the noise reduction (sound attenuation) provided by a semi insert device is described theoretically by the formula $Pa/Pe=As=(Ze+Zs)/Ze$, where Pe is the sound pressure at the entrance of the ear canal, Pa—the sound pressure in the ambient air, As—the sound attenuation, Ze—the acoustic impedance at the entrance of the ear canal, and Zs—the acoustic impedance of the seal provided by the semi insert through which sound must penetrate into the ear canal. If Zs is much larger than Ze, as it should be in effective devices, the formula can be approximated by $As=Zs/Ze$ showing that the sound (noise) attenuation is directly proportional to the acoustic impedance of the seal and inversely proportional to the acoustic impedance at the entrance of the ear canal. According to the present invention, the noise attenuation is increased by placing a relatively small acoustic impedance, Zm, in parallel with the impedance of the ear canal, Ze. When Zm is sufficiently small, the sound attenuation approaches $Asm=Zs/Zm$ and the improvement in sound attenuation, $(Asm/As)=(Ze/Zm)$. In the limit, then, the improvement is proportional to the ratio between the ear canal and the shunting impedances. In practice the effect is somewhat smaller but can be very large, nevertheless.

Structurally, the improvement in sound attenuation is achieved by perforating the semi insert and attaching to it a tube, called the muffler tube, having appropriate dimensions and being open at one end for coupling to the ear canal and closed at the other. Such a tube, when properly designed, can have an acoustic impedance at the open end that is substantially lower than the acoustic input impedance at the entrance of the ear canal.

There are two fundamental ways in which the acoustic impedance at the open end of the muffler tube can be made small compared to that at the entrance of the ear canal. One is to make the inner cross sectional area of the tube substantially larger than that of the ear canal and the tube long enough for its air volume to substantially exceed that of the ear canal, the other, to make the length of the tube equal approximately to a quarter wave length of sound at a desired sound frequency. The effect is the strongest when both methods are combined.

The acoustic impedance near the entrance of the ear canal was measured in the past. According to these measurements it is approximately equal on the average to the acoustic impedance of a volume of air of 1.7 cm³ filled with light damping material. The lowest individual values can reach the acoustic impedance of a volume of air as large as 2.5 cm³. (The acoustic impedance is inversely proportional to the volume.)

A tube with a cross sectional area of 1.15 cm² and a length of 4 cm has an air volume of 4.6 cm³, almost three times as large as the average equivalent volume of the ear canal and somewhat less than twice the largest equivalent volume. Accordingly, it should increase the sound attenuation provided by a semi insert ear defender by a factor of about 2 to 3. This is equal in terms of the more usual logarithmic measure to about 6 to 10 dB, where sound attenuation in decibels is determined by the formula $(Pa/Pe)dB=20 \log(Pa/Pe)$. This increment in sound attenuation is the least that appears worthwhile in view of added cost and bulk. A tube of 4 cm length, closed at one end, has a quarter wave resonance around 2,000 Hz. In this frequency region, the acoustic impedance at the open end of the tube is reduced well below that determined by the air volume in the tube and the sound attenuation further enhanced, the amount depending on sound absorption within the tube. In the same frequency region, the sensitivity of hearing is near its maximum and strong attenuation of ambient noise is highly beneficial.

Lengthening the muffler tube to 25 cm increases its air volume to about 29 cm³ with a concomitant theoretical enhancement of sound attenuation provided by a semi insert device by over 20 dB at low sound frequencies. This enhancement is further increased by a quarter wave resonance around 350 Hz. Such a strong sound attenuation in the low frequency region would be desirable in a noise environment with strong low frequency components.

When, instead of being lengthened, the muffler tube is made wider, so that its cross sectional area amounts to 1.5 cm² and its air volume becomes almost 3.5 times greater than the equivalent volume at the entrance of an average ear canal, it enhances the sound attenuation nominally by about 13 dB on the average and by 10 dB in the case of the largest ear canals. The frequency of the quarter wave resonance remains unchanged, so that the muffler tube still presents to the ear canal the lowest acoustic impedance in the frequency region of 2,000 Hz. However, under many conditions a noise reduction enhancement of a minimum of 10 dB is sufficient, and the quarter wave resonance can be dispensed with. Under such conditions, the muffler tube can be tapered as the distance from its open end increases for better sound transmission from a source terminating the muffler tube or a remote source attached to the muffler tube through an extension tube. Taper of the muffler tube makes it possible to more closely match the acoustic impedance of the source to the tube impedance, making the source work more efficiently.

Muffler tubes with cross sectional areas up to almost 4 $cm^2$ and lengths of about 7 cm have been found suitable. They have allowed sound attenuations of over 40 dB in a wide frequency range, substantially more than has been possible thus far with any commercially available ear defenders.

Instead of being closed at one end, the muffler tube of one ear can be connected at this end to the corresponding end of the muffler tube belonging to the contralateral ear. Under such conditions, a half wave resonance can be achieved, the length of each tube being equal to a quarter wave. Such an arrangement has essentially the same affect on the acoustic impedance at the open ends of the tubes as the quarter wave resonance in each tube separately.

A muffler tube sufficiently wide to achieve the desired noise reduction cannot always be accommodated comfortably in the outer ear at the entrance of the ear canal. It is often necessary to connect it to the ear canal by a narrower tube. For such a tube to interfere as little as possible with the desired acoustic effect of the muffler tube, it must be as short and wide as is compatible with the anatomy of the outer ear around the ear canal entrance. In practice, connecting tubes of 2 cm length and 1 cm inner diameter, equivalent approximately to a cross sectional area of 0.8 $Cm^2$, have been achieved. The acoustic impedance of such a tube is numerically equal to the acoustic impedance of a medium size muffler tube with a volume of air of 10 $cm^3$ at about 1,000 Hz, when the effect of the quarter wave resonance is disregarded. The resonance moves this frequency somewhat downward. The impedance is lower at lower frequencies and higher at the higher ones. This means that the connecting tube interferes little with the muffler tube below 1,000 Hz but has a limiting effect above 1,000 Hz. Nevertheless, the acoustic impedance of such a connecting tube is lower than that at the entrance of the ear canal throughout the useful frequency range for speech communication and music, so that the connecting tube allows the attenuation of ambient noise to be enhanced in this frequency range, even though, the effect is smaller than below 1,000 Hz. Since, even without muffler tubes, semiinsert ear defenders tend to produce acceptable noise reduction above 1,000 Hz, the decreased enhancement effect is not bothersome. It actually may be desirable under many conditions, since it leads to an approximately constant overall reduction of ambient noise throughout the practically useful range of audible sound frequencies. This prevents distortion of useful signals, such as speech and music.

In the frequency region where the acoustic impedances of the muffler tube and the connecting tube are numerically equal, they tend to cancel each other, being of opposite signes, and the residual impedance becomes very small. In this region, the enhancement of noise attenuation is maximum.

It should also be understood that noise reduction at the ear canal entrance does not only depend on the acoustic properties of the muffler tube but also on its seal to the entrance of the ear canal. To maximize the seal without causing unacceptable discomfort, the muffler tube must be connected to the ear canal via an appropriately shaped, preferably soft, perforated plug (semi-insert). The plugs currently used in connection with semi-insert ear defenders are not appropriate because they are either not perforated, or the perforation is much too small. We have found that plugs with a wide perforation equal in size or exceeding the size of the ear canal and consisting either of soft plastic or rubber or of foam plastic are particularly suitable. Such plugs have a configuration of a sleeve or a cuff.

Tubes have been used for sound transmission from a remote source to the ear canal already in the 19th century and, perhaps, even earlier. Currently, they are popular in such applications as the passenger communications systems on commercial air planes and stethoscopes in medicine. They are also used in some hearing aids. Except in the latter, the tubes have to be made rather long, on the order of 60 cm or more. They are made rather narrow, being about equal in cross section to the average ear canal or somewhat narrower. This is done principally for two reasons. First, wider tubes become cumbersome, especially, when they are long. Second, sound transmission to the ear canal is best when the tube has the same cross sectional area as the ear canal. Otherwise, part of sound energy is reflected back into the tube. On this basis, acoustic systems have been devised with the explicit purpose of delivering sound to the ear canal through a tube without any sound reflection either at the junction between the tube and the ear canal or at the end of the tube or within the tube. Accordingly, the tube is made essentially of the same diameter as the ear canal and is open at one end for coupling to the ear canal and terminated at the free end in such a way as to avoid wave reflection. This is achieved in one of several ways. In one, the tube is filled with appropriate sound absorbing material over a sufficient length to prevent the sound from reaching the free end which can be left open ore closed. Since sound energy is not supposed to reach the end, this is immaterial. In another, the tube is tapered toward the free end to make the sound absorption by a sound absorbing material more efficient. In still another, the tube is flaired toward the free end to adapt the tube acoustic impedance to that of open air. In order to avoid wave reflection at the electroacoustic transducer delivering sound to the tube, the transducer is placed not near the free end of the tube but circumferentially, near the ear canal. From the description, it is clear that the system is inadequate for acceptable passive reduction of ambient noise in the ear canal. To achieve such reduction, the tube would have to be substantially wider. This would create wave reflection at the ear canal and defeat the purpose of the system. For this reason, active noise reduction is applied.

When the ear muffler device is used for sound transmission from a sound source, the transmission is reduced by the relatively large inner cross sectional area of the muffler tube and sound reflection at the junction between the tube and the ear canal. However the reduction is modest when the sound source is placed near the closed end of the tube. In this arrangement, the relatively low acoustic impedance of the muffler tube is in series with the relatively high impedance at the entrance of the ear canal and causes little loss of sound energy generated by the source. Since, at the same time reduction of ambient noise is high, the signal to noise ratio is also high, which is the decisive parameter in listening to speech or music or other useful signals.

Figure 2:
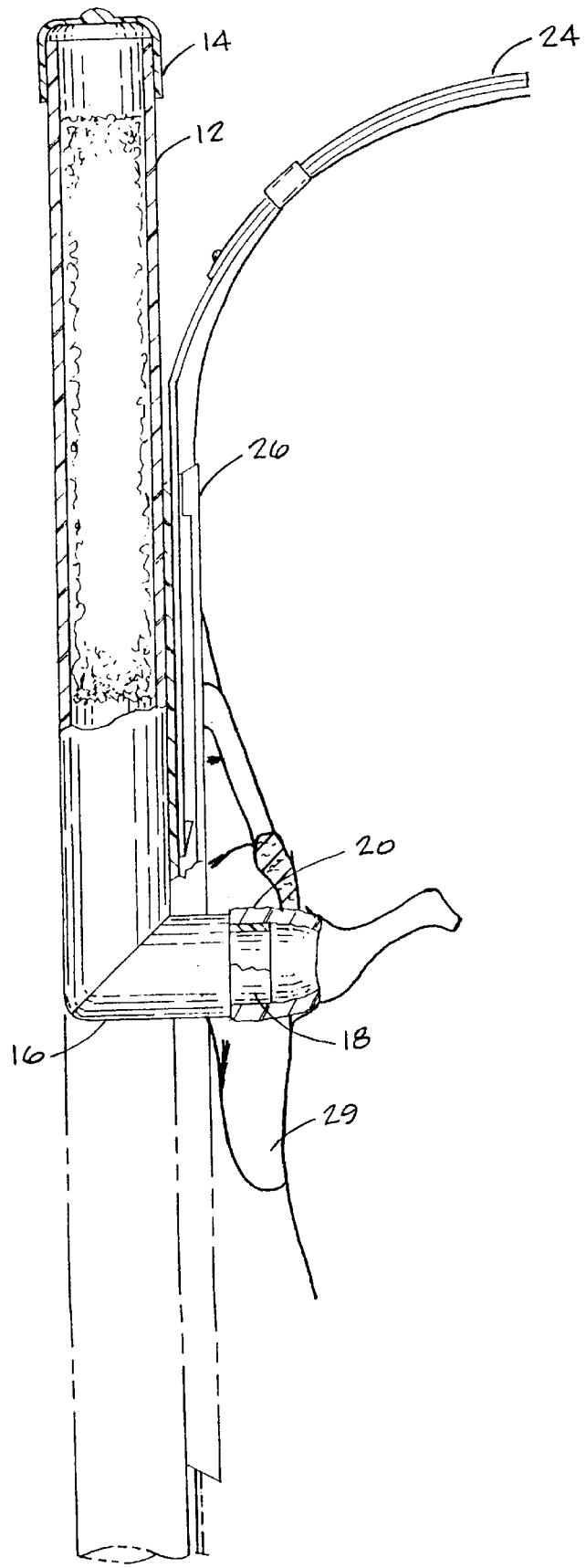
FIG. 2 is a partial side sectional view of the left side of the device of FIG. 1 shown in place on the head.

Referring now to the drawings, FIGS. 1 and 1a illustrate one embodiment of an ear muffler 10 of the present invention which comprises a cylindrical hollow muffler tube 12 closed at one end with the cap 14 and connected to the ear canal through its extension 16 and the connecting tube 18 of a reduced diameter for a better fit to the outer ear. The end of tube 18 defines an opening 28 to provide communication with the outer ear. As shown in FIG. 2, a tight fit of the connecting tube to the ear surface 29 around the ear canal is achieved by means of the soft cuff 20 fastened to the connecting tube 18. The muffler tube 12 is filled with light sound-absorbing material 22 such as cotton, felt or nylon fibers, and is held in place by means of a springy headband 24, adjustably mounted on the tube 12 with the help of the holder 26, firmly attached to the tube 12. To achieve a tight seal around the ear canal entrance, the springy headband is made to gently press the connecting-tube portion 18 against the ear, so as to compress somewhat cuff 20. Only one half of the ear muffler is shown in FIG. 2, the other half being disposed symmetrically on the other side of the head.

The components of the ear muffler may be made of any suitable materials such as plastics, rubbers, and lightweight metals or alloys which are readily available to the art. Typical plastics include polyvinyl chloride (PVC), polyethylene and polypropylene. Silicone rubbers may also be used. Suitable metals include aluminum, aluminum alloys and stainless steel.

In one embodiment, the muffler tube 12 together with its extension 16 measures about 13 cm in length and provides a quarter-wave resonance around 650 Hz, which further increases the ambient-noise reduction in the broad vicinity of this frequency. Decreasing the total length or increasing it, would shift the maximum noise reduction upward or downward in sound frequency. Decreasing or increasing the amount of sound absorbing material 22 would make the maximum more or less pronounced. The tube has a diameter of 1.4 cm, equivalent to a cross sectional area of about 1.5 $cm^2$. Increasing or decreasing it would increase or decrease the amount of sound reduction, respectively. A much wider tube could become cumbersome, however, and a much narrower tube would provide a vanishing amount of noise reduction. It is estimated that a tube with a diameter equal to or smaller than about 1.2 cm, equivalent to a cross sectional area of about 1.15 $cm^2$, would no longer serve usefully the purpose of noise reduction.

A variant of the above described embodiment of the present invention is shown by dashed lines in FIG. 1. Instead of being held in an upright position, the muffler tube hangs from the ear canal in a manner like a stethoscope tube. This position can be obtained without any modification in the construction by simply rotating the ear muffler downward, using the ear canals as axes of rotation. Nevertheless, it will be understood by those versed in the art that a somewhat different construction, specifically adapted to the stethoscope-type configuration can also be used for this embodiment.

Figure 9:
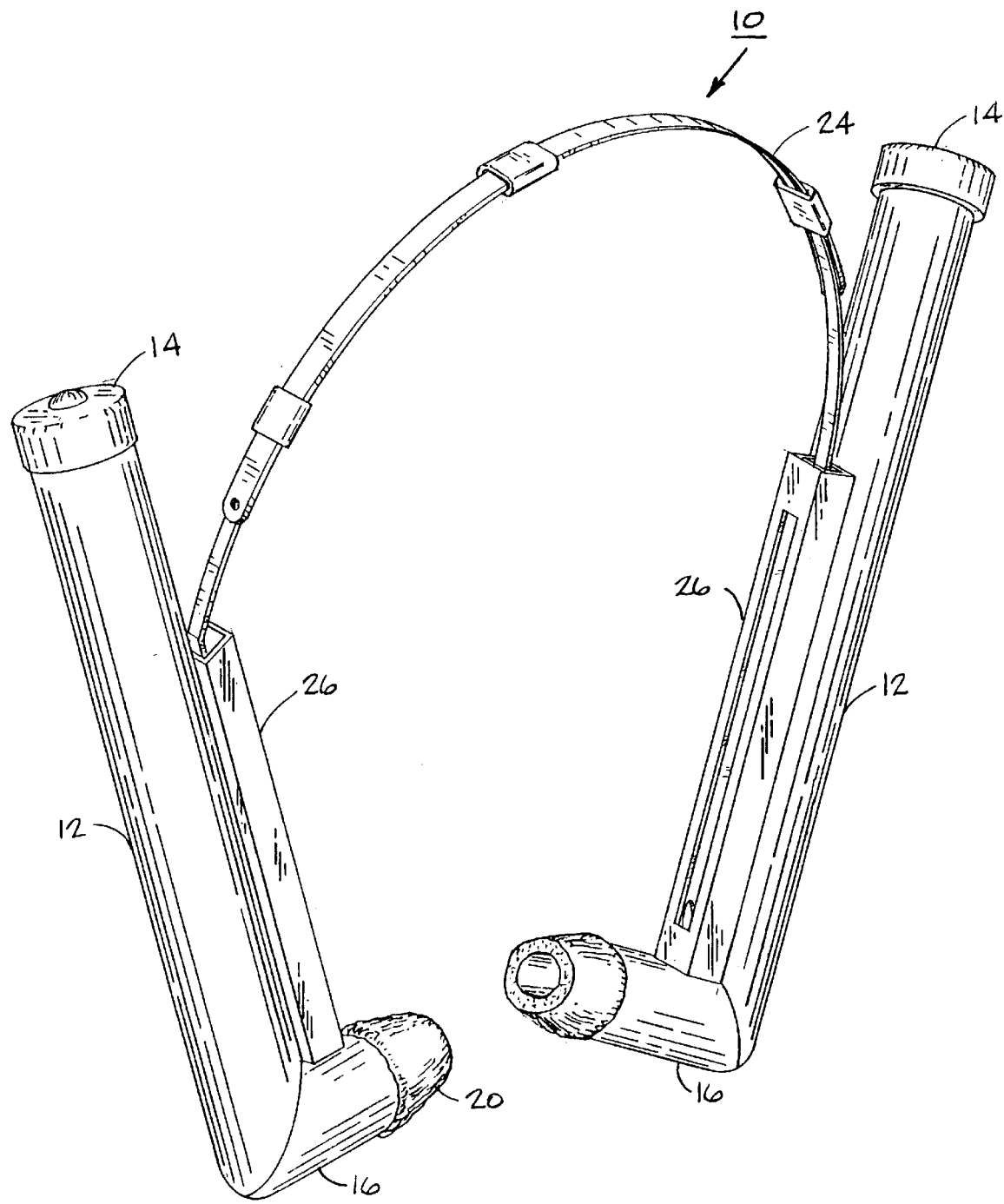
FIG. 9 is a perspective view of the ear muffler device of FIG. 1.

A perspective view of the ear muffler device of FIG. 1 is shown in FIG. 9.

Referring to FIGS. 3 and 3a, the ear muffler 30 uses muffler tubes 32 which are bent at 34 to conform roughly to the shape of the head to make the device less obtrusive than with the straight tubes, 12, in FIGS. 1 and 2.

In a further embodiment shown in FIG. 4, the ear muffler device 40 is designed to allow the muffler tube 42 to have a U configuration to make it more unobtrusive. FIG. 5 illustrates a tapered muffler tube 50 in its hanging position. Such a tapered tube can be made to match the acoustic impedance of the tube to that of a sound source, such as an earphone or a stethoscope end piece, placed at the location indicated by the enlargement 52 for the purpose of improving sound transmission from the source. More generally, the muffler tube can take various shapes and configurations for the purpose of optimum acoustic performance under given noise and signal conditions.

A further embodiment is illustrated in FIG. 6 in which the single muffler tube of FIGS. 1 and 2 is replaced by a set of relatively narrow tubes 60 connected acoustically in parallel for the purpose of achieving the same low acoustic impedance that is obtained with one wide tube. The advantages of the parallel tubes are unobtrusiveness, and more flexibility in the ear muffler configuration. The tubes can be made of different length so that each resonates with a different sound frequency and increases sound attenuation in the neighborhood of this frequency.

In a further embodiment, as shown in FIG. 7, an electroacoustic transducer 72 is placed at the end of the muffler tube 70. The device is screened from the ambient noise by the cap 74 that is separated from the device by a sufficient volume of air 76 so as not to affect destructively the acoustic properties of the device. The device can be powered electrically by an external source via a cable 78 that traverses the cap through a hermetically sealed opening so as not to let the ambient noise in. It is particularly advantageous to attach the transducer at the outer end of the muffler tube since, then, the transfer impedance of the tube is in series with the impedance of the ear, and the loss of the signal power is minimized. This is so, because the tube impedance must be made smaller than the ear impedance for reasons of noise reduction. The loss can be further reduced when a tapered tube is used, and the characteristic impedance of the tube at its free end is matched to the impedance of the transducer. Of course, the transducer must be appropriately sealed against the ambient noise. The same principle can be used for a stethoscope when the stethoscope tube is attached to a muffler tube. For this purpose, an appropriate perforation is made in the closed end of the muffler tube to receive the stethoscope tube. Of course, other sound generating devices can be attached in a similar way. In general, the inner cross sectional area of the stethoscope or similar tubes should not exceed approximately 0.3 $cm^2$, to preserve sufficiently the acoustic properties of the muffler tube.

Another embodiment is illustrated in FIG. 8 in which muffler tube 80 contains an acoustic network consisting of plates 82 having perforations 84 and placed within the muffler tube and supported on a vertical rod 86 for the purpose of affecting the tube's acoustic properties, specifically its input impedance for the purpose of shaping spectrally the noise reduction at the ear canal entrance. A similar effect can be obtained by either leaving air spaces between solid plates and the inner tube wall or introducing constrictions in the muffler tube at appropriate length intervals. Such constrictions give the tube the appearance of a corrugated tube.

While the present invention has been particularly shown and described with reference to the preferred mode, as illustrated in the drawings, it will be understood by one skilled in the art that various changes in detail may be effected therein without departing from the spirit and scope of the invention as defined by the claims.

I claim:

1. A passive ear defender of the semiinsert type which is designed to reduce the level of ambient noise in the ear canal, which comprises:

a tube, called muffler tube, open at one end for coupling to the ear canal through a soft sealing cuff and closed at the other end so as to provide appreciable wave reflection sufficient to produce a quarter-wave resonance below a sound frequency of about 2,000 Hz, said muffler tube having a length of about 4 to 25 centimeters and an inner cross sectional area of at least approximately 1.15 cm$^2$, which is substantially greater than that of the ear canal.

2. The device of claim 1 in which the muffler tube and sealing cuff are separated by a short connecting tube, said connecting tube being as short and wide as is compatible with the anatomy of the outer ear so as to reduce interference with the beneficial acoustic effect of the muffler tube.

3. The device according to claim 1 in which both the muffler tube and the connecting tube are cylindrical in cross section, and the muffler tube has an internal diameter of at least approximately 1.2 cm, equivalent to a cross sectional area of about 1.15 cm$^2$.

4. The device according to claim 1 in which the connecting tube comprises at least in part of a resilient material.

5. The device according to claim 1 in which the muffler tube contains light sound absorbing material for the purpose of regulating the strength of the quarter wave resonance without eliminating it.

6. The device according to claim 1 in which the muffler tube is subdivided internally in its length by perforated plates for the purpose of regulating spectrally the reduction of ambient noise.

7. The device according to claim 1 in which the muffler tube is subdivided internally in its length by plates leaving air spaces between their circumferences and the inner wall of the tube for the purpose of regulating spectrally the reduction of ambient noise.

8. The device according to claim 1 in which the muffler tube has corrugated walls producing a variation in its inner cross sectional area for the purpose of regulating spectrally the reduction of ambient noise, the mean of the variable area being greater than approximately 1.15 cm2.

9. The device according to claim 1 in which the muffler tube is oval in cross section.

10. The device according to claim 1 in which the muffler tube is rectangular in cross section.

11. The device according to claim 1 in which the muffler tube is replaced by a set of tubes connected in parallel and having the same aggregate acoustic input impedance as a single muffler tube.

12. The device according to claim 1 in which the muffler tube is bent so as to conform grossly to the shape of the head.

13. The device according to claim 1 in which the muffler tube is bent according to a U shape.

14. The device according to claim 1 in which the muffler tube belonging to one ear is connected by a spring to the muffler tube belonging to the other ear for the purpose of securing the tubes in the ears.

15. The device according to claim 1 in which the muffler tubes, each belonging to one ear, are held in place on the head by an adjustable headband.

16. The device according to claim 1 in which an earphone is placed within the muffler tube, near its closed end, and is isolated from the ambient air.

17. The device according to claim 1 in which the closed end of the muffler tube has a relatively small perforation designed to receive a tube of no more than approximately 0.3 cm$^2$ inner cross sectional area for sound transmission from a remote source.

18. The device according to claim 17 in which the remote sound source consists of a stethoscope.

19. A passive ear defender of the semiinsert type designed to reduce the level of ambient noise in the ear canal, which comprises:

a tube, called muffler tube, open at one end for coupling to the ear canal through a short connecting tube and a soft sealing cuff and connected at the other end to a sound source isolated from ambient air, said muffler tube having an inner cross sectional area of at least approximately 1.5 cm$^2$, said connecting tube being as short and wide as is compatible with the anatomy of the outer ear so as to reduce interference with the beneficial acoustic effect of the muffler tube.

20. The device according to claim 19 in which the cross sectional area of the muffler tube is at least approximately 1.5 cm2 at the open end but decreases as the distance from the open end increases.

21. A passive ear defender of the semi-insert type which is designed to reduce the level of ambient noise in the ear canal, which comprises:

a tube, called muffler tube, open at one end for coupling to the ear canal through a short connecting tube and a soft sealing cuff, said muffler tube having an inner cross sectional area of at least approximately 1.15 cm2 and being connected at its other end to an identical muffler tube belonging to the contralateral ear without an appreciable change in inner cross sectional area for the purpose of producing a half wave resonance below 1,500 Hz, said connecting tube being as short and wide as is compatible with the anatomy of the outer ear so as to reduce interference with the beneficial acoustic effect of the muffler tube.

22. A method for the reduction of ambient noise in the ear, which comprises:

(a) providing an elongated air filled muffler tube closed at one end but open at the other and having an acoustic input impedance at the open end which is substantially smaller than the acoustic impedance at the entrance of the ear canal over a wide range of sound frequencies, the open end of the tube shaped for coupling to the ear canal with a resilient sealing cuff mounted on the tube at its open end for the purpose of tightly coupling the tube to the ear canal; and (b) securing said tube in the ear through said sealing cuff whereby ambient noise in the ear is significantly reduced.

* * * * *